(12) United States Patent
Johnson et al.

(10) Patent No.: US 10,058,394 B2
(45) Date of Patent: Aug. 28, 2018

(54) ROBOT ARM AND METHODS OF USE

(71) Applicant: GLOBUS MEDICAL, INC., Audubon, PA (US)

(72) Inventors: Norbert Johnson, North Andover, MA (US); Timothy Moulton, Newport, RI (US); Michael Bartelme, Fort Collins, CO (US); Rasool Khadem, Superior, CO (US); Neil R. Crawford, Chandler, AZ (US)

(73) Assignee: GLOBUS MEDICAL, INC., Audubon, PA (US)

( * ) Notice: Subject to any disclaimer, the term of this patent is extended or adjusted under 35 U.S.C. 154(b) by 385 days.

(21) Appl. No.: 14/815,198

(22) Filed: Jul. 31, 2015

(65) Prior Publication Data

US 2017/0027652 A1    Feb. 2, 2017

(51) Int. Cl.
| | |
|---|---|
| *A61B 34/30* | (2016.01) |
| *A61B 90/50* | (2016.01) |
| *A61B 90/00* | (2016.01) |
| *A61B 34/20* | (2016.01) |

(52) U.S. Cl.
CPC .............. *A61B 34/30* (2016.02); *A61B 90/50* (2016.02); *A61B 2034/2055* (2016.02); *A61B 2034/2057* (2016.02); *A61B 2090/064* (2016.02); *A61B 2090/376* (2016.02); *A61B 2090/3762* (2016.02); *Y10S 901/09* (2013.01); *Y10S 901/23* (2013.01)

(58) Field of Classification Search
CPC ...................................................... G05B 19/423
USPC ................................................... 700/257, 264
See application file for complete search history.

(56) References Cited

U.S. PATENT DOCUMENTS

| | | | |
|---|---|---|---|
| 7,904,206 B2 * | 3/2011 | Shioda | A61B 34/75 700/245 |
| 8,123,675 B2 | 2/2012 | Funda et al. | |
| 8,509,503 B2 * | 8/2013 | Nahum | A61B 34/70 382/128 |
| 9,339,934 B2 * | 5/2016 | Kogan | B25J 9/1656 |
| 2009/0259412 A1 * | 10/2009 | Brogardh | B25J 9/1633 702/41 |
| 2013/0184871 A1 * | 7/2013 | Fudaba | B25J 13/02 700/264 |
| 2014/0222023 A1 | 8/2014 | Kim et al. | |
| 2015/0066051 A1 | 3/2015 | Kwon et al. | |

FOREIGN PATENT DOCUMENTS

| | | |
|---|---|---|
| WO | 2009123891 A1 | 10/2009 |
| WO | 2011058530 A1 | 5/2011 |

* cited by examiner

*Primary Examiner* — Timothy R Waggoner

(57) ABSTRACT

A robot arm and method for using the robot arm. Embodiments may be directed to an apparatus comprising: a robot arm; an end effector coupled at a distal end of the robot arm and configured to hold a surgical tool; a plurality of motors operable to move the robot arm; and an activation assembly operable to send a move signal allowing an operator to move the robot arm.

13 Claims, 14 Drawing Sheets

ROBOT ARM AND METHODS OF USE

BACKGROUND

Embodiments are directed to a robot arm and, more particularly, a robot arm that may assist surgeons with medical tools in an operation.

Various medical procedures require the precise localization of a three-dimensional position of a surgical instrument within the body in order to effect optimized treatment. For example, some surgical procedures to fuse vertebrae require that a surgeon drill multiple holes into the bone structure at specific locations. To achieve high levels of mechanical integrity in the fusing system, and to balance the forces created in the bone structure, it is necessary that the holes are drilled at the correct location. Vertebrae, like most bone structures, have complex shapes made up of non-planar curved surfaces making precise and perpendicular drilling difficult. Conventionally, a surgeon manually holds and positions a drill guide tube by using a guidance system to overlay the drill tube's position onto a three dimensional image of the bone structure. This manual process is both tedious and time consuming. The success of the surgery is largely dependent upon the dexterity of the surgeon who performs it.

Robotic systems have been employed to help reduce tedious and time consuming processes. Many of the current robots used in surgical applications are specifically intended for magnifying/steadying surgical movements or providing a template for milling the bone surface. However, these robots are suboptimal for drilling holes and other related tasks.

Consequently, there is a need for a robot system that minimizes human and robotic error while allowing fast and efficient surgical access. The ability to perform operations on a patient with a robot system will greatly diminish the adverse effects upon the patient. The application of the robot system and the techniques used with the robot system may enhance the overall surgical operation and the results of the operation.

SUMMARY

Embodiments may be directed to an apparatus comprising: a robot arm; an end effector coupled at a distal end of the robot arm and configured to hold a surgical tool; a plurality of motors operable to move the robot arm; and an activation assembly operable to send a move signal allowing an operator to move the robot arm.

Embodiments may be directed to a method of moving a robot arm comprising: depressing a primary button on an activation assembly; applying force to the activation assembly; sensing the force with a load cell; communicating force to a computer processor; activating motors within robot arm using the computer processor; and moving the robot arm with the motors in the direction of the applied force.

Embodiments may be directed to a method of moving a robot arm comprising: depressing a primary button on an activation assembly; applying force to the activation assembly; moving the robot arm with the motors in the direction of the applied force; moving the robot arm to a gravity well; and stopping the robot arm in the gravity well.

BRIEF DESCRIPTION OF THE DRAWINGS

For a detailed description of the preferred embodiments of the invention, reference will now be made to the accompanying drawings in which.

DETAILED DESCRIPTION

Figure 1:
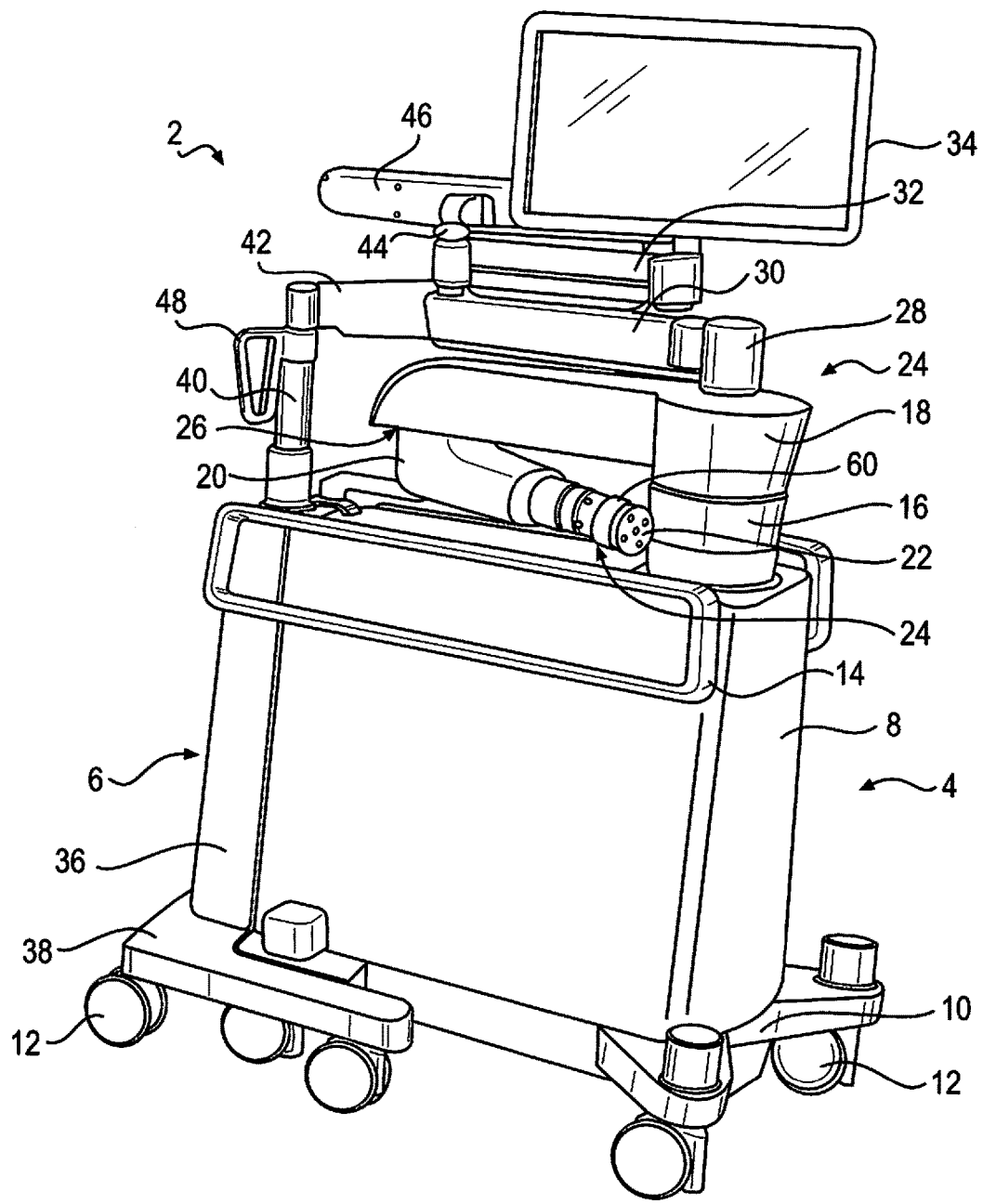
FIG. 1 illustrates an embodiment of an automated medical system.

FIG. 1 illustrates an embodiment of an automated medical system 2. Prior to performance of an invasive medical procedure, a three-dimensional ("3D") image scan may be taken of a desired surgical area of a patient and sent to a computer platform in communication with an automated medical system 2. In some embodiments, a physician may then program a desired point of insertion and trajectory for a surgical instrument to reach a desired anatomical target within or upon the body of the patient. In some embodiments, the desired point of insertion and trajectory may be planned on the 3D image scan, which in some embodiments, may be displayed on a display. In some embodiments, a physician may plan the trajectory and desired insertion point (if any) on a computed tomography scan (hereinafter referred to as "CT scan") of the patient. In some embodiments, the CT scan may be an isocentric C-arm type scan, an O-arm type scan, or intraoperative CT scan as is known in the art. However, in some embodiments, any known 3D image scan may be used in accordance with the embodiments of automated medical system 2.

A medical procedure may begin with automated medical system 2 moving from medical storage to a medical procedure room. Automated medical system 2 may be maneuvered through doorways, halls, and elevators to reach a medical procedure room. Within the room, automated medical system 2 may be physically separated into two separate and distinct systems, a robot support system 4 and a camera tracking system 6. Robot support system 4 may be positioned adjacent the patient at any suitable location to properly assist medical personnel. Camera tracking system 6 may be positioned at the base of the patient or any other location suitable to track movement of robot support system 4 and the patient. Robot support system 4 and camera tracking system 6 may be powered by an onboard power source and/or plugged into an external wall outlet.

Automated medical system 2, as illustrated in FIG. 1, may assist surgeons and doctors during medical procedures. Automated medical system 2 may assist surgeons and doctors by holding tools, aligning tools, using tools, guiding tools, and/or positioning tools for use. In embodiments, as illustrated in FIG. 1, automated medical system 2 may comprise of a robot support system 4 and a camera tracking system 6. Both systems may be coupled together by any suitable means. Suitable means may be, but are not limited to mechanical latches, ties, clamps, or buttresses, or magnetic or magnetized surfaces. The ability to combine robot support system 4 and camera tracking system 6 may allow for automated medical system 2 to maneuver and move as a single unit. This combination may allow automated medical system 2 to have a small footprint in an area, allow easier movement through narrow passages and around turns, and allow storage within a smaller area.

Robot support system 4 may be used to assist a surgeon by holding and/or using tools during a medical procedure. To properly utilize and hold tools, robot support system 4 may rely on a plurality of motors, computers, and/or actuators to function properly. Illustrated in FIG. 1, robot body 8 may act as the structure in which the plurality of motors, computers, and/or actuators may be secured within robot support system 4. Robot body 8 may also provide support for robot telescoping support arm 16. In embodiments, robot body 8 may be made of any suitable material. Suitable material may be, but is not limited to, metal such as titanium, aluminum, or stainless steel, carbon fiber, fiberglass, or heavy-duty plastic. The size of robot body 8 may provide a solid platform on which other components may connect and operate. Robot body 8 may house, conceal, and protect the plurality of motors, computers, and/or actuators that may operate attached components.

Robot base 10 may act as a lower support for robot support system 4. In embodiments, robot base 10 may support robot body 8 and may attach robot body 8 to a plurality of powered wheels 12. This attachment to wheels may allow robot body 8 to move in space efficiently. Robot base 10 may run the length and width of robot body 8. Robot base 10 may be about two inches to about 10 inches tall. Robot base 10 may be made of any suitable material. Suitable material may be, but is not limited to, metal such as titanium, aluminum, or stainless steel, carbon fiber, fiberglass, or heavy-duty plastic or resin. Robot base 10 may cover, protect, and support powered wheels 12.

In embodiments, as illustrated in FIG. 1, at least one powered wheel 12 may be attached to robot base 10. Powered wheels 12 may attach to robot base 10 at any location. Each individual powered wheel 12 may rotate about a vertical axis in any direction. A motor may be disposed above, within, or adjacent to powered wheel 12. This motor may allow for automated medical system 2 to maneuver into any location and stabilize and/or level automated medical system 2. A rod, located within or adjacent to powered wheel 12, may be pressed into a surface by the motor. The rod, not pictured, may be made of any suitable metal to lift automated medical system 2. Suitable metal may be, but is not limited to, stainless steel, aluminum, or titanium. Additionally, the rod may comprise at the contact-surface-side end a buffer, not pictured, which may prevent the rod from slipping and/or create a suitable contact surface. The material may be any suitable material to act as a buffer. Suitable material may be, but is not limited to, a plastic, neoprene, rubber, or textured metal. The rod may lift powered wheel 10, which may lift automated medical system 2, to any height required to level or otherwise fix the orientation of the automated medical system 2 in relation to a patient. The weight of automated medical system 2, supported through small contact areas by the rod on each wheel, prevents automated medical system 2 from moving during a medical procedure. This rigid positioning may prevent objects and/or people from moving automated medical system 2 by accident.

Moving automated medical system 2 may be facilitated using robot railing 14. Robot railing 14 provides a person with the ability to move automated medical system 2 without grasping robot body 8. As illustrated in FIG. 1, robot railing 14 may run the length of robot body 8, shorter than robot body 8, and/or may run longer the length of robot body 8. Robot railing 14 may be made of any suitable material. Suitable material may be, but is not limited to, metal such as titanium, aluminum, or stainless steel, carbon fiber, fiberglass, or heavy-duty plastic. Robot railing 14 may further provide protection to robot body 8, preventing objects and or personnel from touching, hitting, or bumping into robot body 8.

Robot body 8 may provide support for a Selective Compliance Articulated Robot Arm, hereafter referred to as a "SCARA." A SCARA 24 may be beneficial to use within the automated medical system due to the repeatability and compactness of the robotic arm. The compactness of a SCARA may provide additional space within a medical procedure, which may allow medical professionals to perform medical procedures free of excess clutter and confining areas. SCARA 24 may comprise robot telescoping support 16, robot support arm 18, and/or robot arm 20. Robot telescoping support 16 may be disposed along robot body 8. As illustrated in FIG. 1, robot telescoping support 16 may provide support for the SCARA 24 and display 34. In embodiments, robot telescoping support 16 may extend and contract in a vertical direction. Robot telescoping support 16 may be made of any suitable material. Suitable material may be, but is not limited to, metal such as titanium or stainless steel, carbon fiber, fiberglass, or heavy-duty plastic. The body of robot telescoping support 16 may be any width and/or height in which to support the stress and weight placed upon it. In embodiments, medical personnel may move SCARA 24 through a command submitted by the medical personnel. The command may originate from input received on display 34 and/or a tablet. The command may come from the depression of a switch and/or the depression of a plurality of switches. Best illustrated in FIGS. 4 and 5, an activation assembly 60 may comprise a switch and/or a plurality of switches. The activation assembly 60 may be operable to transmit a move command to the SCARA 24 allowing an operator to manually manipulate the SCARA 24. When the switch, or plurality of switches, is depressed the medical personnel may have the ability to move SCARA 24 easily. Additionally, when the SCARA 24 is not receiving a command to move, the SCARA 24 may lock in place to prevent accidental movement by personnel and/or other objects. By locking in place, the SCARA 24 provides a solid platform upon which an end effector 22 and end effector tool 26 may be used during a medical operation.

Robot support arm 18 may be disposed on robot telescoping support 16 by any suitable means. Suitable means may be, but is not limited to, nuts and bolts, ball and socket fitting, press fitting, weld, adhesion, screws, rivets, clamps, latches, and/or any combination thereof. In embodiments, best seen in FIGS. 1 and 2, robot support arm 18 may rotate in any direction in regard to robot telescoping support 16. Robot support arm 18 may rotate three hundred and sixty degrees around robot telescoping support 16. Robot arm 20 may connect to robot support arm 18 at any suitable location. Robot arm 20 may attach to robot support arm 16 by any suitable means. Suitable means may be, but is not limited to, nuts and bolts, ball and socket fitting, press fitting, weld, adhesion, screws, rivets, clamps, latches, and/or any combination thereof. Robot arm 20 may rotate in any direction in regards to robot support arm 18, in embodiments, robot arm 20 may rotate three hundred and sixty degrees in regards to robot support arm 18. This free rotation may allow an operator to position robot arm 20 as desired.

Figure 4:
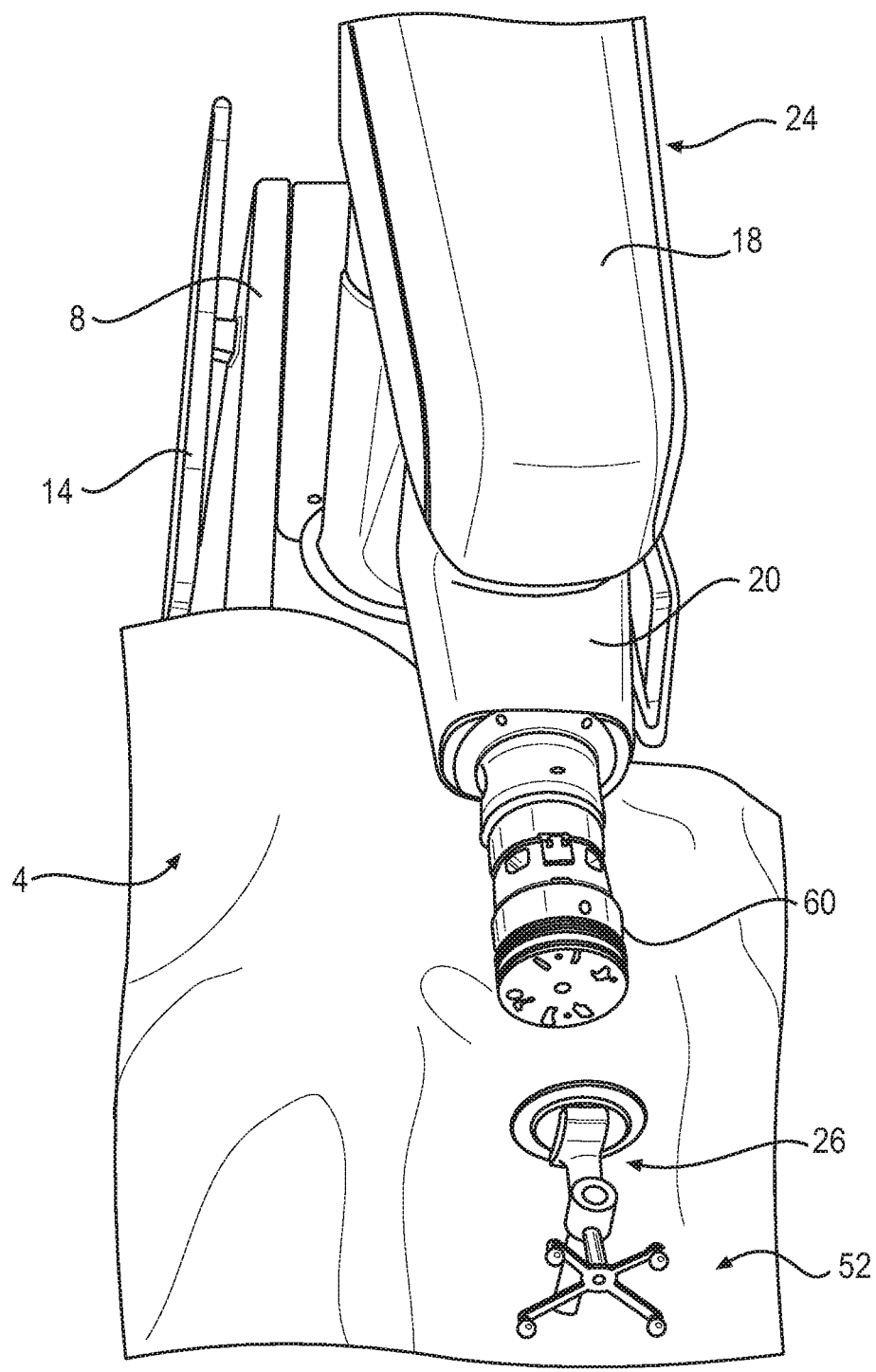
FIG. 4 illustrates an embodiment of a SCARA with end effector.

End effector 22 may attach to robot arm 20 in any suitable location. End effector 22 may attach to robot arm 20 by any suitable means. Suitable means may be, but is not limited to, latch, clamp, nuts and bolts, ball and socket fitting, press fitting, weld, adhesion, screws, rivets, and/or any combination thereof. End effector 22 may move in any direction in relation to robot arm 20. This freedom of directionality may allow a user to move end effector 22 to a desired area. An end effector tool 26, as illustrated in FIG. 4 may attach to end effector 22. End effector tool 26 may be any tool selected for a medical procedure. End effector tool 26 may be disposed and removed from end effector 22 by any suitable means. Suitable means may be, but is not limited to, clamp, latch, tie, press fit, or magnet. In embodiments, end effector tool 26 may have a dynamic reference array 52. Dynamic reference arrays 52, herein referred to as "DRAs", are rigid bodies which may be disposed on a patient and/or tool in a navigated surgical procedure. Their purpose may be to allow 3D localization systems to track the positions of tracking markers that are embedded in the DRA 52, and thereby track the real-time position of relevant anatomy. Tracking markers may be seen, recorded, and/or processed by camera 46. This tracking of 3D coordinates of tracking markers may allow automated medical system 2 to find the DRA 52 in any space in relation to a patient 50.

As illustrated in FIG. 1, a light indicator 28 may be positioned on top of the SCARA 24. Light indicator 28 may illuminate as any type of light to indicate "conditions" in which automated medical system 2 is currently operating. For example, the illumination of green may indicate that all systems are normal. Illuminating red may indicate that automated medical system 2 is not operating normally. A pulsating light may mean automated medical system 2 is performing a function. Combinations of light and pulsation may create a nearly limitless amount of combinations in which to communicate the current operating "conditions." In embodiments, the light may be produced by LED bulbs, which may form a ring around light indicator 28. Light indicator 28 may comprise a fully permeable material that may let light shine through the entirety of light indicator 28. In embodiments, light indicator 28 may only allow a ring and/or designated sections of light indicator 28 to allow light to pass through.

Figure 2:
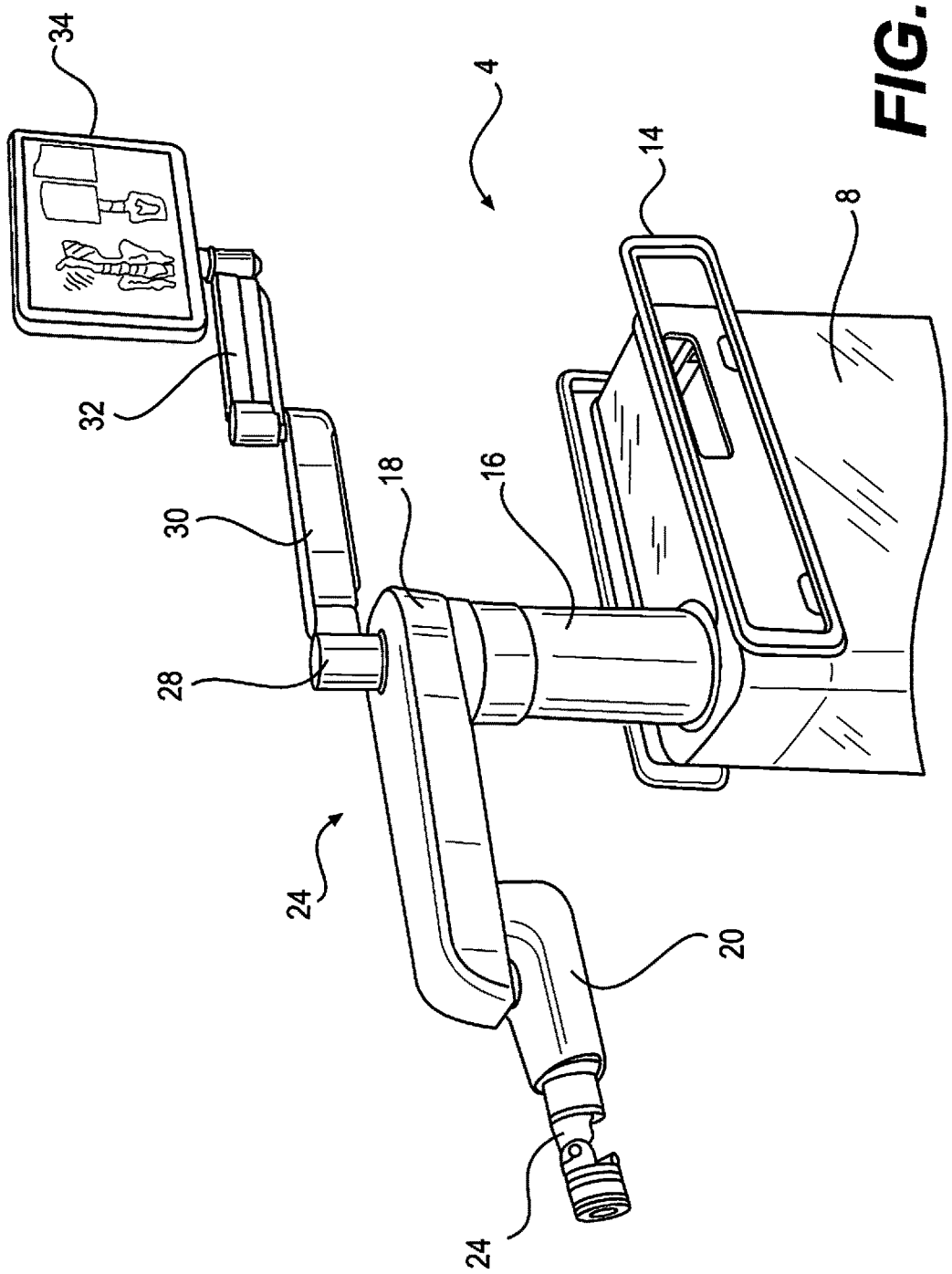
FIG. 2 illustrates an embodiment of a robot support system.

Light indicator 28 may be attached to lower display support 30. Lower display support 30, as illustrated in FIG. 2 may allow an operator to maneuver display 34 to any suitable location. Lower display support 30 may attach to light indicator 28 by any suitable means. Suitable means may be, but is not limited to, latch, clamp, nuts and bolts, ball and socket fitting, press fitting, weld, adhesion, screws, rivets, and/or any combination thereof. In embodiments, lower display support 30 may rotate about light indicator 28. In embodiments, lower display support 30 may attach rigidly to light indicator 28. Light indicator 28 may then rotate three hundred and sixty degrees about robot support arm 18. Lower display support 30 may be of any suitable length, a suitable length may be about eight inches to about thirty four inches. Lower display support 30 may act as a base for upper display support 32.

Upper display support 32 may attach to lower display support 30 by any suitable means. Suitable means may be, but are not limited to, latch, clamp, nuts and bolts, ball and socket fitting, press fitting, weld, adhesion, screws, rivets, and/or any combination thereof. Upper display support 32 may be of any suitable length, a suitable length may be about eight inches to about thirty four inches. In embodiments, as illustrated in FIG. 1, upper display support 32 may allow display 34 to rotate three hundred and sixty degrees in relation to upper display support 32. Likewise, upper display support 32 may rotate three hundred and sixty degrees in relation to lower display support 30.

Display 34 may be any device which may be supported by upper display support 32. In embodiments, as illustrated in FIG. 2, display 34 may produce color and/or black and white images. The width of display 34 may be about eight inches to about thirty inches wide. The height of display 34 may be about six inches to about twenty two inches tall. The depth of display 34 may be about one-half inch to about four inches.

In embodiments, a tablet may be used in conjunction with display 34 and/or without display 34. In embodiments, the table may be disposed on upper display support 32, in place of display 34, and may be removable from upper display support 32 during a medical operation. In addition the tablet may communicate with display 34. The tablet may be able to connect to robot support system 4 by any suitable wireless and/or wired connection. In embodiments, the tablet may be able to program and/or control automated medical system 2 during a medical operation. When controlling automated medical system 2 with the tablet, all input and output commands may be duplicated on display 34. The use of a tablet may allow an operator to manipulate robot support system 4 without having to move around patient 50 and/or to robot support system 4.

Figure 5:
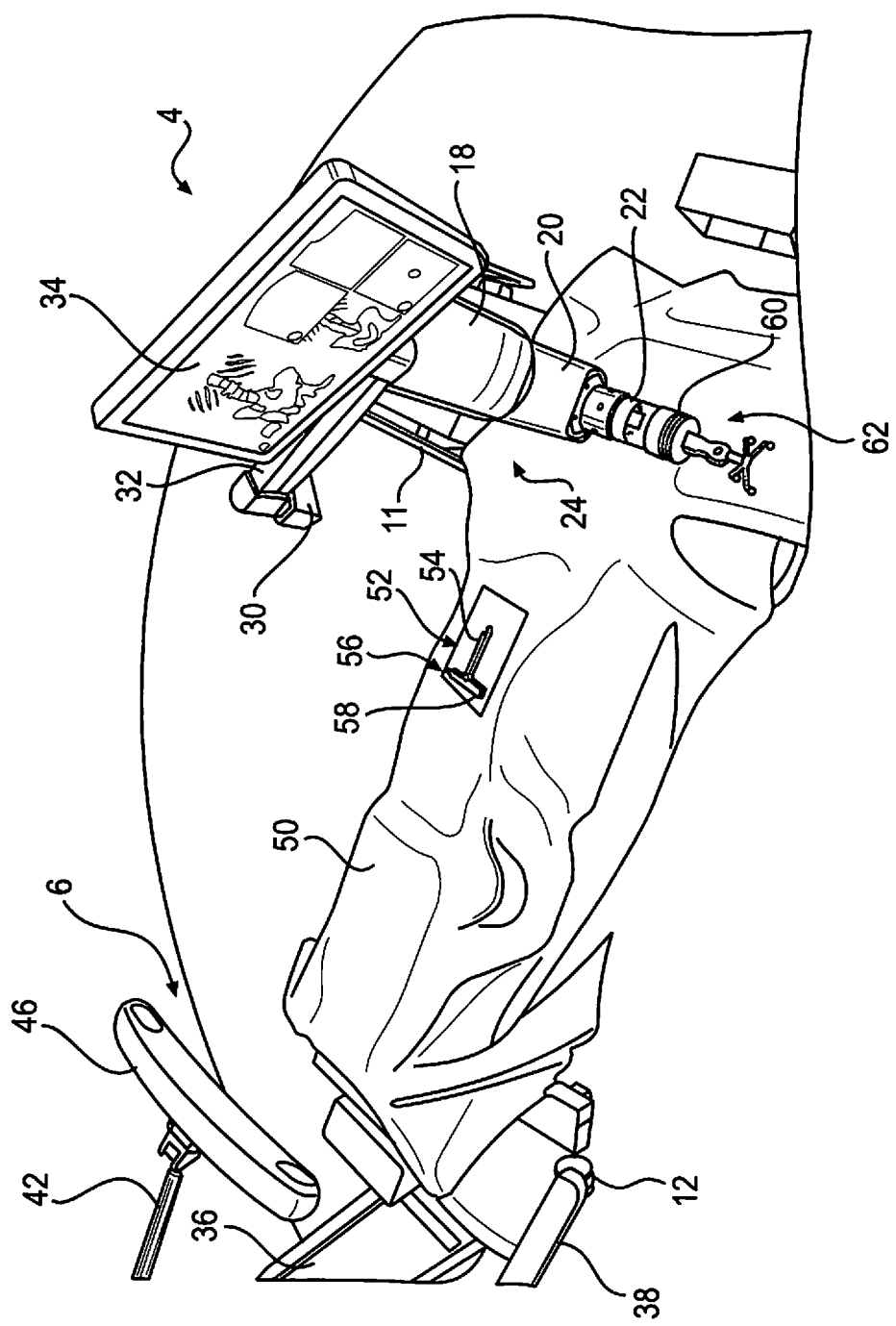
FIG. 5 illustrates an embodiment of a medical operation in which a robot support system and a camera system are disposed around a patient.

As illustrated in FIG. 5, camera tracking system 6 may work in conjunction with robot support system 4. Described above, camera tracking system 6 and robot support system 4 may be able to attach to each other. Camera tracking system 6, now referring to FIG. 1, may comprise similar components of robot support system 4. For example, camera body 36 may provide the functionality found in robot body 8. Robot body 8 may provide the structure upon which camera 46 may be mounted. The structure within robot body 8 may also provide support for the electronics, communication devices, and power supplies used to operate camera tracking system 6. Camera body 36 may be made of the same material as robot body 8. Camera tracking system 6 may also communicate with robot support system 4 by any suitable means. Suitable means may be, but are not limited to, a wired or wireless connection. Additionally, camera tracking system 6 may communicate directly to the table by a wireless and/or wired connection. This communication may allow the tablet to control the functions of camera tracking system 6.

Camera body 36 may rest upon camera base 38. Camera base 38 may function as robot base 10. In embodiments, as illustrated in FIG. 1, camera base 38 may be wider than robot base 10. The width of camera base 38 may allow for camera tracking system 6 to connect with robot support system 4. As illustrated in FIG. 1, the width of camera base 38 may be large enough to fit outside robot base 10. When camera tracking system 6 and robot support system 4 are connected, the additional width of camera base 38 may allow automated medical system 2 additional maneuverability and support for automated medical system 2.

As with robot base 10, a plurality of powered wheels 12 may attach to camera base 38. Powered wheel 12 may allow camera tracking system 6 to stabilize and level or set fixed orientation in regards to patient 50, similar to the operation of robot base 10 and powered wheels 12. This stabilization may prevent camera tracking system 6 from moving during a medical procedure and may keep camera 46 from losing track of DRA 52 within a designated area. This stability and maintenance of tracking may allow robot support system 4 to operate effectively with camera tracking system 6. Additionally, the wide camera base 38 may provide additional support to camera tracking system 6. Specifically, a wide camera base 38 may prevent camera tracking system 6 from tipping over when camera 46 is disposed over a patient, as illustrated in FIG. 5. Without the wide camera base 38, the outstretched camera 46 may unbalance camera tracking system 6, which may result in camera tracking system 6 falling over.

Camera telescoping support 40 may support camera 46. In embodiments, telescoping support 40 may move camera 46 higher or lower in the vertical direction. Telescoping support 40 may be made of any suitable material in which to support camera 46. Suitable material may be, but is not limited to, metal such as titanium, aluminum, or stainless steel, carbon fiber, fiberglass, or heavy-duty plastic. Camera handle 48 may be attached to camera telescoping support 40 at any suitable location. Cameral handle 48 may be any suitable handle configuration. A suitable configuration may be, but is not limited to, a bar, circular, triangular, square, and/or any combination thereof. As illustrated in FIG. 1, camera handle 48 may be triangular, allowing an operator to move camera tracking system 6 into a desired position before a medical operation. In embodiments, camera handle 48 may be used to lower and raise camera telescoping support 40. Camera handle 48 may perform the raising and lowering of camera telescoping support 40 through the depression of a button, switch, lever, and/or any combination thereof.

Lower camera support arm 42 may attach to camera telescoping support 40 at any suitable location, in embodiments, as illustrated in FIG. 1, lower camera support arm 42 may rotate three hundred and sixty degrees around telescoping support 40. This free rotation may allow an operator to position camera 46 in any suitable location. Lower camera support arm 42 may be made of any suitable material in which to support camera 46. Suitable material may be, but is not limited to, metal such as titanium, aluminum, or stainless steel, carbon fiber, fiberglass, or heavy-duty plastic. Cross-section of lower camera support arm 42 may be any suitable shape. Suitable cross-sectional shape may be, but is not limited to, circle, square, rectangle, hexagon, octagon, or i-beam. The cross-sectional length and width may be about one to ten inches. Length of the lower camera support arm may be about four inches to about thirty-six inches. Lower camera support arm 42 may connect to telescoping support 40 by any suitable means. Suitable means may be, but is not limited to, nuts and bolts, ball and socket fitting, press fitting, weld, adhesion, screws, rivets, clamps, latches, and/or any combination thereof. Lower camera support arm 42 may be used to provide support for camera 46. Camera 46 may be attached to lower camera support arm 42 by any suitable means. Suitable means may be, but is not limited to, nuts and bolts, ball and socket fitting, press fitting, weld, adhesion, screws, rivets, and/or any combination thereof. Camera 46 may pivot in any direction at the attachment area between camera 46 and lower camera support arm 42. In embodiments a curved rail 44 may be disposed on lower camera support arm 42.

Figure 3:
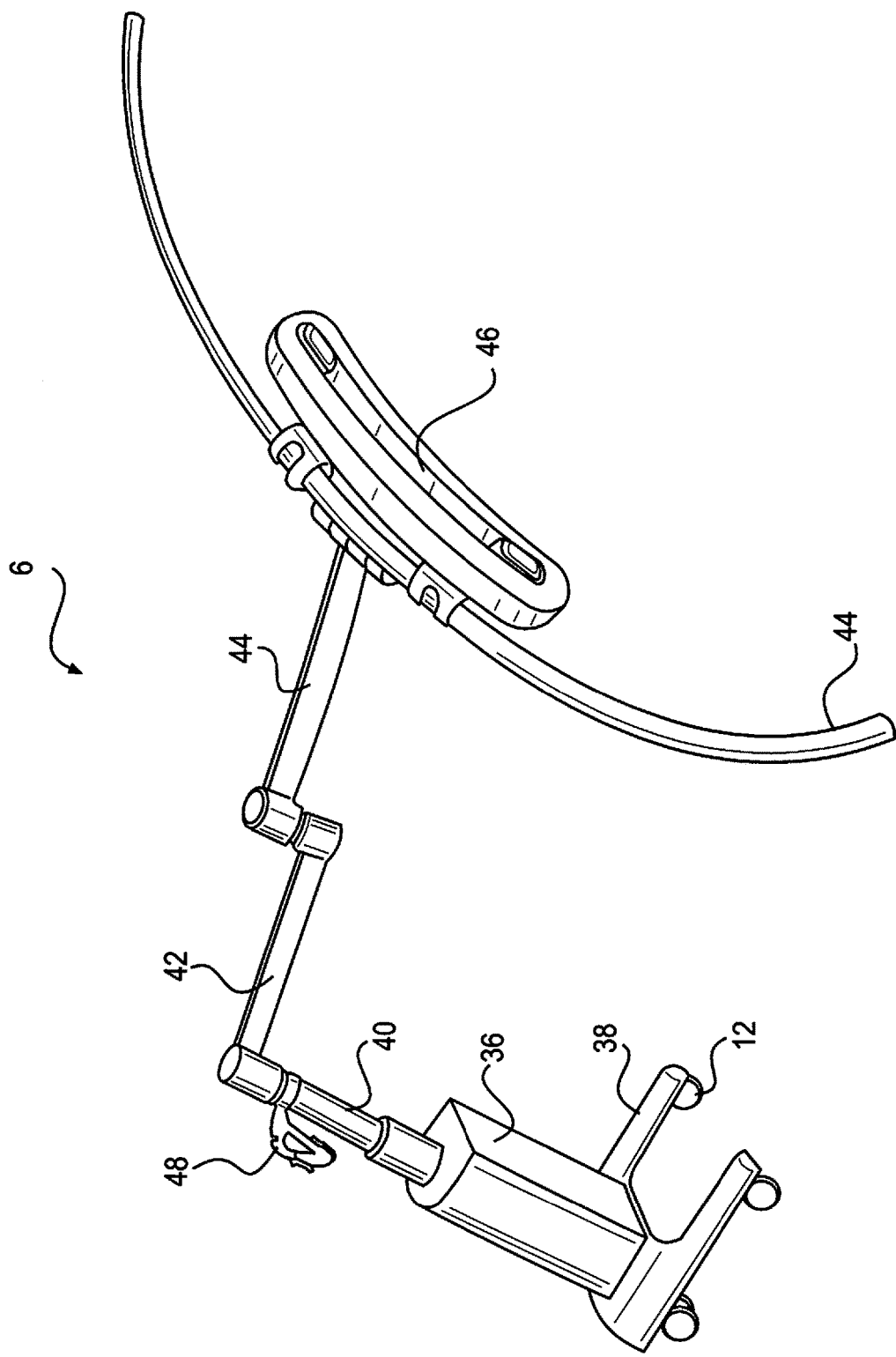
FIG. 3 illustrates an embodiment of a camera tracking system.

Curved rail 44 may be disposed at any suitable location on lower camera support arm 42. As illustrated in FIG. 3, curved rail 44 may attach to lower camera support arm 42 by any suitable means. Suitable means may be, but are not limited to nuts and bolts, ball and socket fitting, press fitting, weld, adhesion, screws, rivets, clamps, latches, and/or any combination thereof. Curved rail 44 may be of any suitable shape, a suitable shape may be a crescent, circular, oval, elliptical, and/or any combination thereof. In embodiments, curved rail 44 may be any appropriate length. An appropriate length may be about one foot to about six feet. Camera 46 may be moveably disposed along curved rail 44. Camera 46 may attach to curved rail 44 by any suitable means. Suitable means may be, but are not limited to, rollers, brackets, braces, motors, and/or any combination thereof. Motors and rollers, not illustrated, may be used to move camera 46 along curved rail 44. As illustrated in FIG. 3, during a medical procedure, if an object prevents camera 46 from viewing one or more DRAs 52, the motors may move camera 46 along curved rail 44 using rollers. This motorized movement may allow camera 46 to move to a new position that is no longer obstructed by the object without moving camera tracking system 6. While camera 46 is obstructed from viewing DRAs 52, camera tracking system 6 may send a stop signal to robot support system 4, display 34, and/or a tablet. The stop signal may prevent SCARA 24 from moving until camera 46 has reacquired DRAs 52. This stoppage may prevent SCARA 24 and/or end effector 22 from moving and/or using medical tools without being tracked by automated medical system 2.

Figure 6:
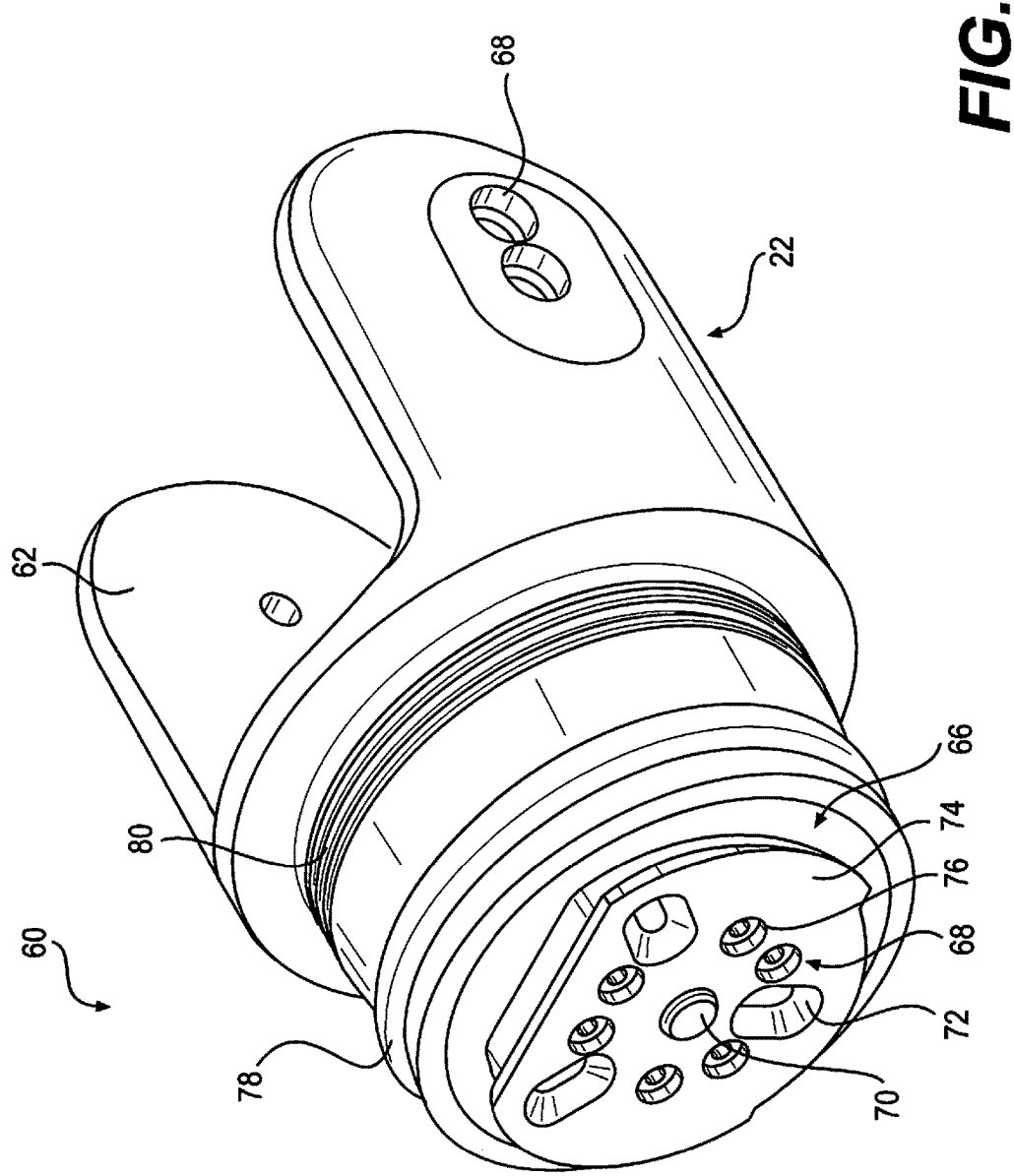
FIG. 6 illustrates an embodiment of an end effector.

End effector 22, as illustrated in FIG. 6, may be used to connect surgical tools to robot support system 4. End effector 22 may comprise a saddle joint 62, an activation assembly 60, a load cell 64, and a tool connection 66. Saddle joint 62 may attach end effector 22 to SCARA 24. Saddle joint 62 may be made of any suitable material. Suitable material may be, but is not limited to metal such as titanium, aluminum, or stainless steel, carbon fiber, fiberglass, or heavy-duty plastic. Saddle joint 62 may be made of a single piece of metal which may provide end effector with additional strength and durability. In examples saddle joint 62 may attach to SCARA 24 by an attachment point 68. There may be a plurality of attachment points 68 disposed about saddle joint 62. Attachment points 68 may be sunk, flush, and/or disposed upon saddle joint 62. In examples, screws, nuts and bolts, and/or any combination thereof may pass through attachment point 68 and secure saddle joint 62 to SCARA 24. The nuts and bolts may connect saddle joint 62 to a motor, not illustrated, within SCARA 24. The motor may move saddle joint 62 in any direction. The motor may further prevent saddle joint 62 from moving from accidental bumps and/or accidental touches by actively servoing at the current location or passively by applying spring actuated brakes. Saddle joint 62 may provide the base upon which a load cell 64 and a tool connection 66 may be disposed.

Figure 7:
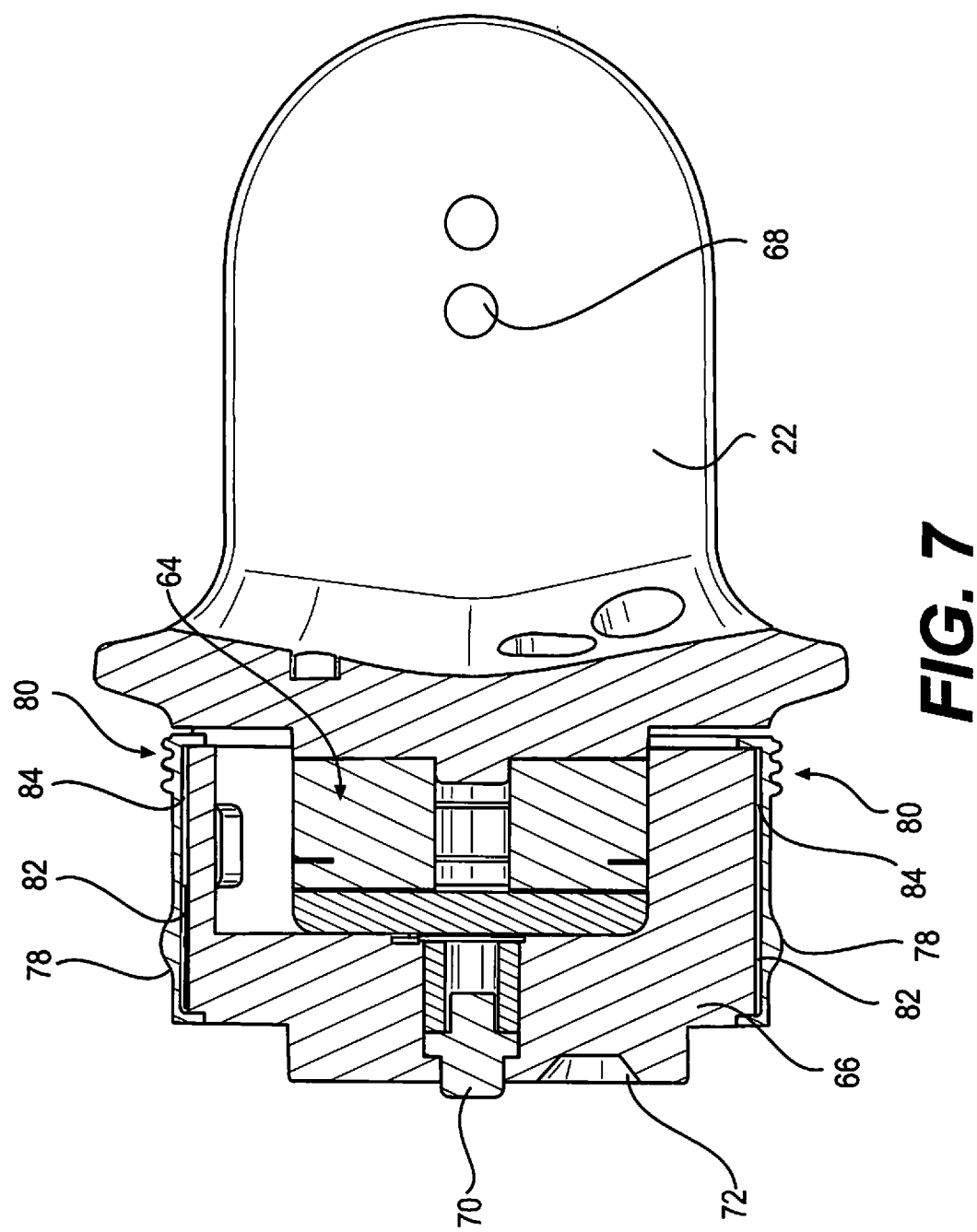
FIG. 7 illustrates an embodiment of a cut away of an end effector.
Figure 8:
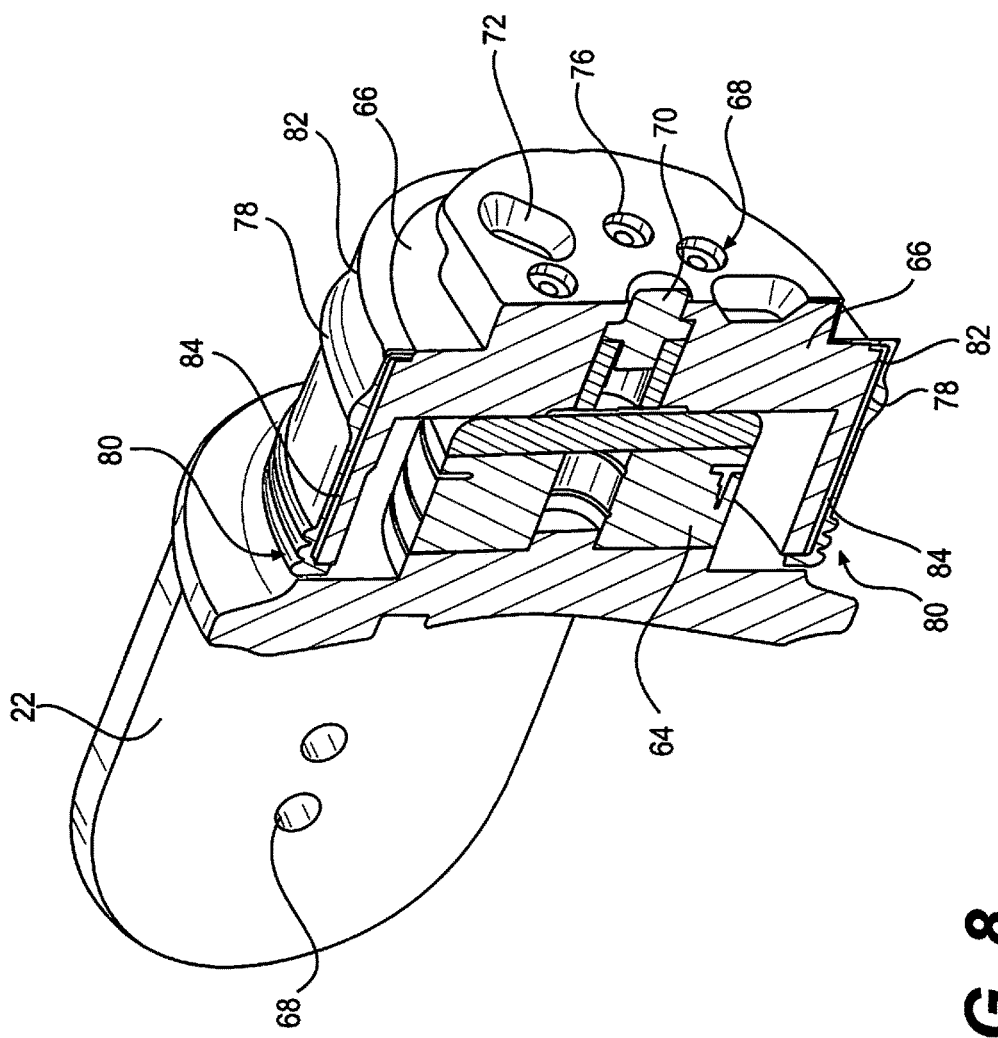
FIG. 8 illustrates an embodiment of a perspective view of an end effector cut away.

Load cell 64, as illustrated in FIGS. 7 and 8 may attach to saddle joint 62 by any suitable means. Suitable means may be, but is not limited to, screws, nuts and bolts, threading, press fitting, and/or any combination thereof. Load cell 64 may be any suitable instrument used to detect and measurement movement. In examples, load cell 64 may be a six axis load cell, a three-axis load cell or a uniaxial load cell. Load cell 64 may be used to track the force applied to end effector 22. As illustrated in FIG. 17, a schematic may show the communication between load cell 64 and a motor 120. In embodiments a load cell 64 may communicate with a plurality of motors 120. As load cell 64 senses force, information as to the amount of force applied may be distributed from a switch array 122 and/or a plurality of switch arrays to a microcontroller unit 122. Microcontroller unit 124 may take the force information from load cell 64 and process it with a switch algorithm. The switch algorithm may allow microcontroller unit 124 to communicate with a motor driver 126. A motor driver 126 may control the function of a motor 120, with which motor driver 126 may communicate. Motor driver 126 may direct specific motors 120 to produce an equal amount of force measured by load cell 64 through motor 120. In embodiments, the force produced may come from a plurality of motors 120, as directed by microcontroller unit 124. Additionally, motor driver 126 may receive input from motion controller 128. Motion controller 128 may receive information from load cell 64 as to the direction of force sensed by load cell 64. Motion controller 128 may process this information using a motion controller algorithm. The algorithm may be used to provide information to specific motor drivers 126. To replicate the direction of force, motion controller 128 may activate and/or deactivate certain motor drivers 126. Working in unison and/or separately, microcontroller unit 124 and motion controller 128 may control motor 120 (or a plurality of motors 120) to induce motion in the direction of force sensed by load cell 64. This force-controlled motion may allow an operator to move SCARA 24 and end effector 22 effortlessly and/or with very little resistance. Movement of end effector 22 may position tool connection 66 in any suitable location for use by medical personnel.

Tool connection 66 may attach to load cell 64. Tool connection 66 may comprise attachment points 68, a sensory button 70, tool guides 72, and/or tool connections 74. Best illustrated in FIGS. 6 and 8, there may be a plurality of attachment points 68. Attachment points 68 may connect tool connection 66 to load cell 64. Attachment points 68 may be sunk, flush, and/or disposed upon tool connection 66. Connectors 76 may use attachment points 68 to attach tool connection 66 to load cell 64. In examples, connectors 76 may be screws, nuts and bolts, press fittings, and/or any combination thereof.

As illustrated in FIG. 6, a sensory button 70 may be disposed about center of tool connection 66. Sensory button 70 may be depressed when an end effector tool 26, best illustrated in FIG. 4, is connected to end effector 22. Depression of sensory button 70 may alert robot support system 4, and in turn medical personnel, that an end effector tool 26 has been attached to end effector 22. As illustrated in FIG. 6, tool guides 72 may be used to facilitate proper attachment of end effector tool 26 to end effector 22. Tool guides 72 may be sunk, flush, and/or disposed upon tool connection 66. In examples there may be a plurality of tool guides 72 and may have any suitable patterns and may be oriented in any suitable direction. Tool guides 72 may be any suitable shape to facilitate attachment of end effector tool 26 to end effector 22. A suitable shape may be, but is not limited to, circular, oval, square, polyhedral, and/or any combination thereof. Additionally, tool guides 72 may be cut with a bevel, straight, and/or any combination thereof.

Tool connection 66 may have attachment points 74. As illustrated in FIG. 6, attachment points 74 may form a ledge and/or a plurality of ledges. Attachment points 74 may provide end effector tool 26 a surface upon which end effector tool 26 may clamp. In examples, attachment points 74 may be disposed about any surface of tool connection 66 and oriented in any suitable manner in relation to tool connection 66.

Tool connection 66 may further serve as a platform for activation assembly 60. Activation assembly 60, best illustrated in FIGS. 6 and 8, may encircle tool connection 66. In embodiments, activation assembly 60 may take the form of a bracelet. As bracelet, activation assembly 60 may wrap around tool connection 66. In embodiments, activation assembly 60, may be located in any suitable area within automated medical system 2. In examples, activation assembly 60 may be located on any part of SCARA 24, any part of end effector 22, may be worn by medical personnel (and communicate wirelessly), and/or any combination thereof. Activation assembly 60 may be made of any suitable material. Suitable material may be, but is not limited to neoprene, plastic, rubber, gel, carbon fiber, fabric, and/or any combination thereof. Activation assembly 60 may comprise of a primary button 78 and a secondary button 80. Primary button 78 and secondary button 80 may encircle the entirety of tool connection 66. Primary button 78 may be a single ridge, as illustrated in FIG. 6, which may encircle tool connection 66. In examples, primary button 78 may be disposed upon activation assembly 60 along the end farthest away from saddle joint 62. Primary button 78 may be disposed upon primary activation switch 82, best illustrated on FIG. 7. Primary activation switch 82 may be disposed between tool connection 66 and activation assembly 60. In examples, there may be a plurality of primary activation switches 82, which may be disposed adjacent and beneath primary button 78 along the entire length of primary button 78. Depressing primary button 78 upon primary activation switch 82 may allow an operator to move SCARA 24 and end effector 22. As discussed above, once set in place, SCARA 24 and end effector 22 may not move until an operator programs robot support system 4 to move SCARA 24 and end effector 22, or is moved using primary button 78 and primary activation switch 82. In examples, it may require the depression of at least two non-adjacent primary activation switches 82 before SCARA 24 and end effector 22 will respond to commands. Depression of at least two primary activation switches 82 may prevent the accidental movement of SCARA 24 and end effector 22 during a medical procedure.

Activated by primary button 78 and primary activation switch 82, load cell 64 may measure the force magnitude and/or direction exerted upon end effector 22 by medical personnel. This information may be transferred to motors within SCARA 24 that may be used to move SCARA 24 and end effector 22. Information as to the magnitude and direction of force measured by load cell 64 may cause the motors to move SCARA 24 and end effector 22 in the same direction as sensed by load cell 64. This force-controlled movement may allow the operator to move SCARA 24 and end effector 22 easily and without large amounts of exertion due to the motors moving SCARA 24 and end effector 22 at the same time the operator is moving SCARA 24 and end effector 22.

Secondary button 80, as illustrated in FIG. 6, may be disposed upon the end of activation assembly 60 closest to saddle joint 62. In examples secondary button 80 may comprise a plurality of ridges. The plurality of ridges may be disposed adjacent to each other and may encircle tool connection 66. Additionally, secondary button 80 may be disposed upon secondary activation switch 84. Secondary activation switch 84, as illustrated in FIG. 7, may be disposed between secondary button 80 and tool connection 66. In examples, secondary button 80 may be used by an operator as a "selection" device. During a medical operation, robot support system 4 may notify medical personnel to certain conditions by display 34 and/or light indicator 28. Medical personnel may be prompted by robot support system 4 to select a function, mode, and/or asses the condition of automated medical system 2. Depressing secondary button 80 upon secondary activation switch 84 a single time may activate certain functions, modes, and/or acknowledge information communicated to medical personnel through display 34 and/or light indicator 28. Additionally, depressing secondary button 80 upon secondary activation switch 84 multiple times in rapid succession may activate additional functions, modes, and/or select information communicated to medical personnel through display 34 and/or light indicator 28. In examples, at least two non-adjacent secondary activation switches 84 may be depressed before secondary button 80 may function properly. This requirement may prevent unintended use of secondary button 80 from accidental bumping by medical personnel upon activation assembly 60. Primary button 78 and secondary button 80 may use software architecture 86 to communicate commands of medical personnel to automated medical system 2.

Figure 9:
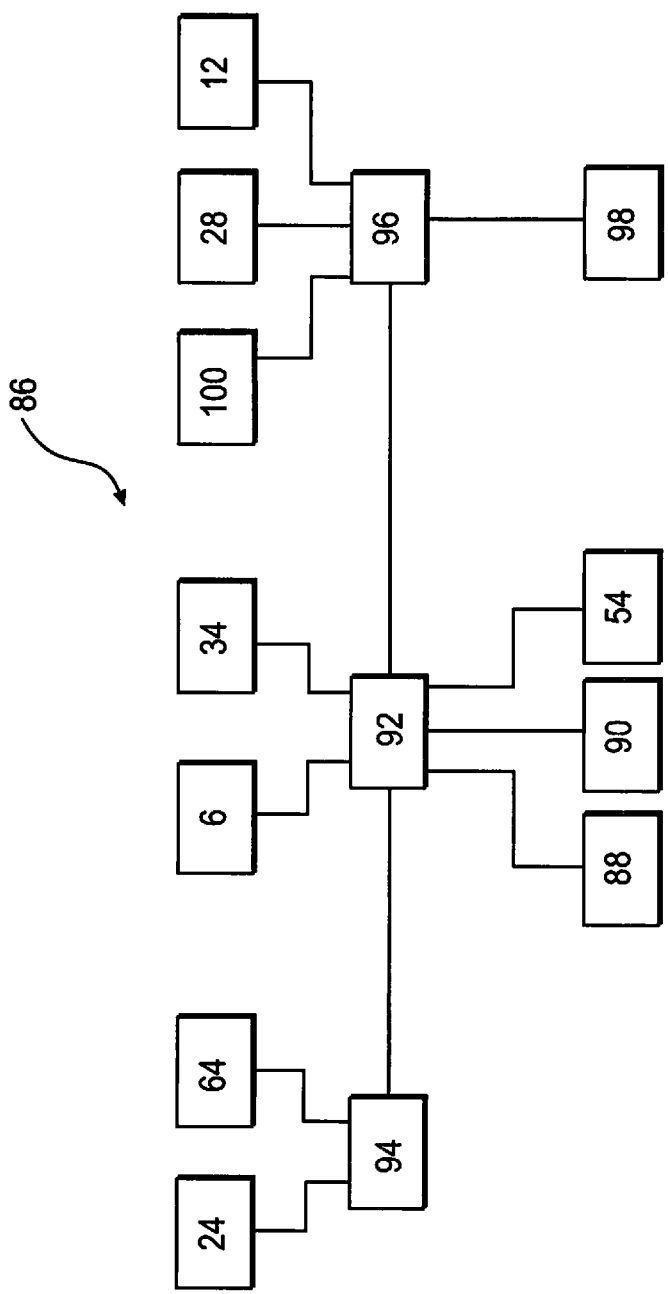
FIG. 9 illustrates an embodiment of a schematic of software architecture used in an automated medical system.

FIG. 9 illustrates a flow chart of software architecture 86 which may be used within automated medical system 2. Software architecture 86 may be used to automated robot support system 4 and camera tracking system 6. Additionally, software architecture 86 may allow an operator to manipulate automated medical system 2 based upon commands given from the operator. In examples, operator commands may comprise Picture Archival and Communication Systems (PACS) 88 (which may communicate with automated imaging system 104, discussed below), USB Devices 90, and commands from tablet 54. These operator commands may be received and transferred throughout automated medical system 2 by a computer processor 92. Computer processor 92 may be able to receive all commands and manipulate automated medical system 2 accordingly. In examples, computer processor 92 may be able to control and identify the location of individual parts that comprise automated medical system 2. Communicating with camera tracking system 6 and display 34, computer processor 92 may be able to locate a patient, end effector 22, and robot support system 4 in a defined space (e.g., illustrated in FIG. 5). Additionally, computer processor 92 may be able to use commands from display 34 and camera tracking system 6 to alter the positions of SCARA 24. Information from load cell 64, based upon measured force magnitude and direction, may be processed by computer processor 92 and sent to motors within SCARA 24, as discussed above. A General Algebraic Modeling System (GAMS) 94 may translate information regarding force magnitude and direction from load cell 64 to electronic signals which may be useable by computer processor 92. This translation may allow computer processor 92 to track the location and movement of robot support system 4 in a defined space when SCARA 24 and end effector 22 are moving. Computer processor 92 may further use firmware 96 to control commands and signals from robot body 8. Firmware 96 may comprise commands that are hardwired to automated medical system 2. For example, computer processor 92 may require power from power supply 98 to operate. Firmware 96 may control the distribution of power from power supply 98 to automated medical system 2. Additionally, computer processor 92 may control firmware 96 and the power distribution based on operator commands. In examples, firmware 96 may communicate with light indicator 28, powered wheels 12, and platform interface 100. Platform interface 100 may be a series of hardwired button commands that directly control automated medical system 2. Button commands are not limited to but may comprise functions that may move automated medical system 2 in any direction, initiate an emergency stop, initiate movement of SCARA 24, and/or communicate current system functionality to medical personnel. Computer processor 92 may process and distribute all operator commends to perform programmed tasks by medical personnel.

Figure 10:
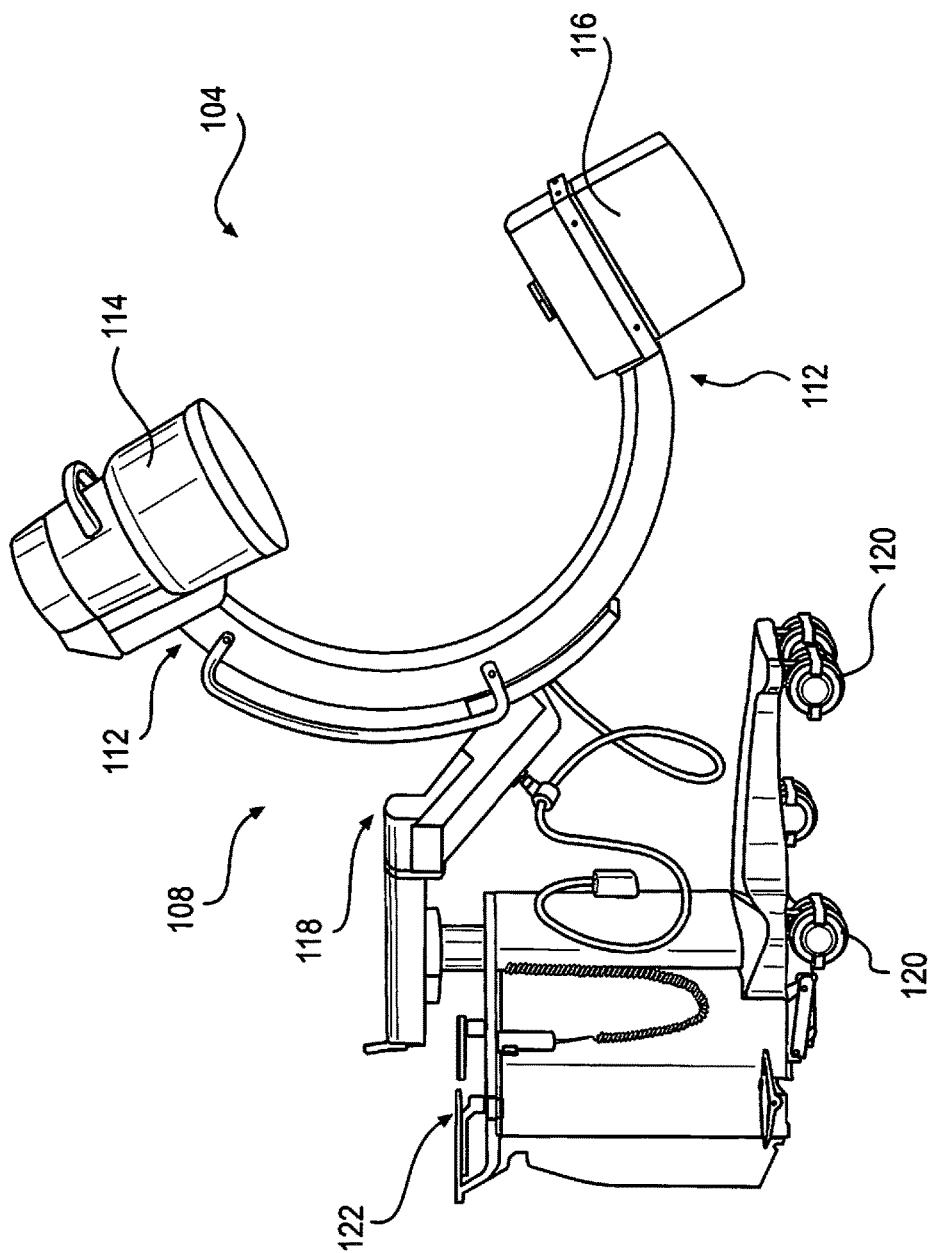
FIG. 10 illustrates an embodiment of a C-Arm imaging device.

Automated imaging system 104 may be used in conjunction with automated medical system 2 to acquire pre-operative, intra-operative, post-operative, and/or real-time image data of patient 50. Any appropriate subject matter may be imaged for any appropriate procedure using automated imaging system 104. In embodiments, automated imaging system 104 may be an O-arm® 106 and/or a C-arm 108 device. (O-arm® is copyrighted by Medtronic Navigation, Inc. having a place of business in Louisville, Colo., USA) It may be desirable to take x-rays of patient 50 from a number of different positions, without the need for frequent manual repositioning of patient 50 which may be required in an x-ray system. C-arm 108 x-ray diagnostic equipment may solve the problems of frequent manual repositioning and may be well known in the medical art of surgical and other interventional procedures. As illustrated in FIG. 10, a C-arm 108 may comprise an elongated C-shaped member 110 terminating in opposing distal ends 112 of the "C" shape. C-shaped member 110 may further comprise an x-ray source 114 and an image receptor 116, which may be mounted at or near distal ends 112, respectively, of C-arm 108 in opposing orientation, with C-arm 108 supported in a suspended position. The space within C-arm 108 of the arm may provide room for the physician to attend to the patient substantially free of interference from x-ray support structure 118. X-ray support structure 118 may rest upon wheels 120, which may enable C-arm 108 to be wheeled from room to room and further along the length of patient 50 during a medical procedure. X-ray images produced from C-arm 108 may be used in an operating room environment to help ensure that automated medical system 2 may be properly positioned during a medical procedure.

C-arm 108 may be mounted to enable rotational movement of the arm in two degrees of freedom, (i.e. about two perpendicular axes in a spherical motion). C-arm 108 may be slidably mounted to x-ray support structure 118, which may allow orbiting rotational movement of C-arm 108 about its center of curvature, which may permit selective orientation of x-ray source 114 and image receptor 116 vertically and/or horizontally. C-arm 108 may also be laterally rotatable, (i.e. in a perpendicular direction relative to the orbiting direction to enable selectively adjustable positioning of x-ray source 114 and image receptor 116 relative to both the width and length of patient 50). Spherically rotational aspects of C-arm 108 apparatus may allow physicians to take x-rays of patient 50 at an optimal angle as determined with respect to the particular anatomical condition being imaged. In embodiments a C-arm 108 may be supported on a wheeled support cart 120. In embodiments an O-arm® 106 may be used separately and/or in conjunction with C-arm 108.

Figure 11:
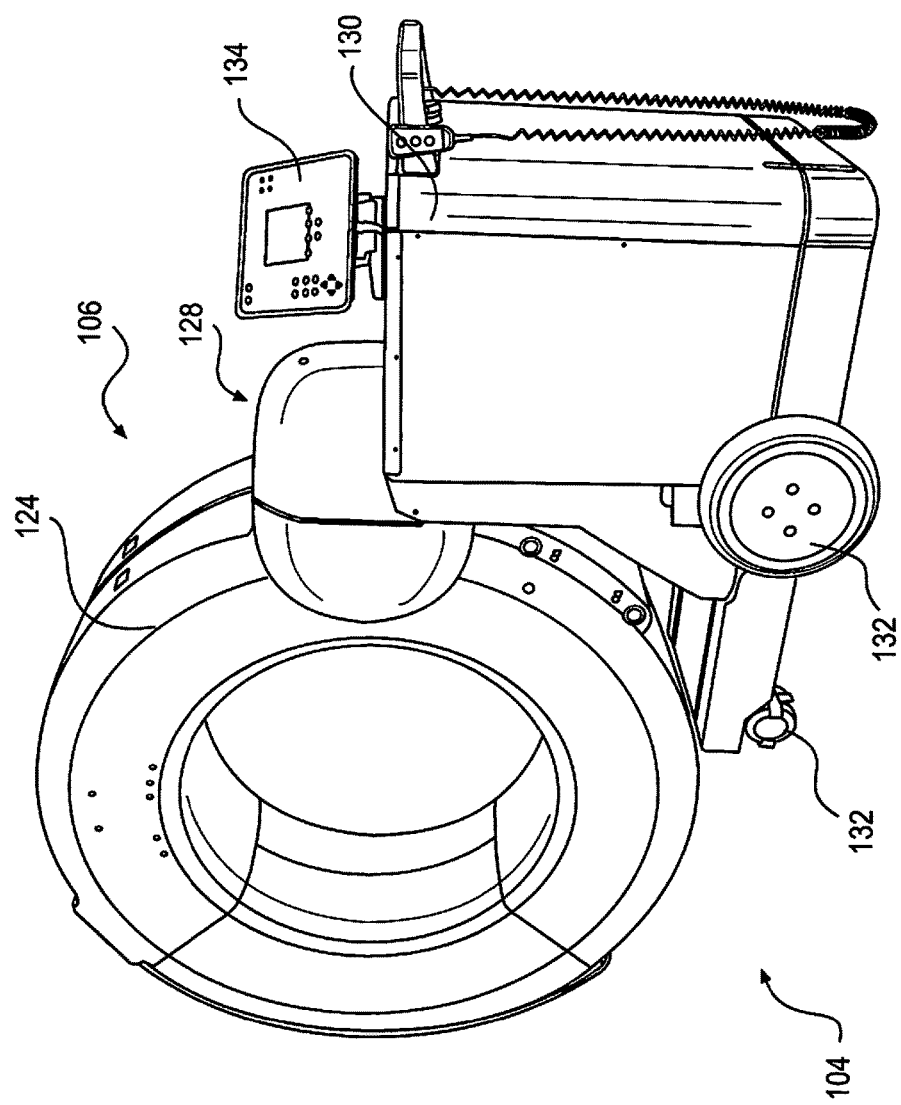
FIG. 11 illustrates an embodiment of a O-Arm® imaging device.

An O-arm® 106, as illustrated in FIG. 11, may comprise a gantry housing 124, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 50 to be acquired from multiple directions or in multiple planes.

In embodiments O-arm® 106 may comprise a gantry housing 124 having a central opening 126 for positioning around an object to be imaged, a source of radiation that is rotatable around the interior of gantry housing 124, which may be adapted to project radiation from a plurality of different projection angles. A detector system may be adapted to detect the radiation at each projection angle to acquire object images from multiple projection planes in a quasi-simultaneous manner. In embodiments, a gantry may be attached to a support structure O-arm® support structure 128, such as a wheeled mobile cart 130 with wheels 132, in a cantilevered fashion. A positioning unit 134 may translate and/or tilt the gantry to a desired position and orientation, preferably under control of a computerized motion control system. The gantry may include a source and detector disposed opposite one another on the gantry. The source and detector may be secured to a motorized rotor, which may rotate the source and detector around the interior of the gantry in coordination with one another. The source may be pulsed at multiple positions and orientations over a partial and/or full three hundred and sixty degree rotation for multi-planar imaging of a targeted object located inside the gantry. The gantry may further comprise a rail and bearing system for guiding the rotor as it rotates, which may carry the source and detector. Both and/or either O-arm® 106 and C-arm 108 may be used as automated imaging system 104 to scan patient 50 and send information to automated medical system 2.

Automated imaging system 104 may communicate with automated medical system 2 before, during, and/or after imaging has taken place. Communication may be performed through hard wire connections and/or wireless connections. Imaging may be produced and sent to automated medical system 2 in real time. Images captured by automated imaging system 104 may be displayed on display 34, which may allow medical personnel to locate bone and organs within a patient. This localization may further allow medical personnel to program automated medical system 2 to assist during a medical operation.

Figure 12:
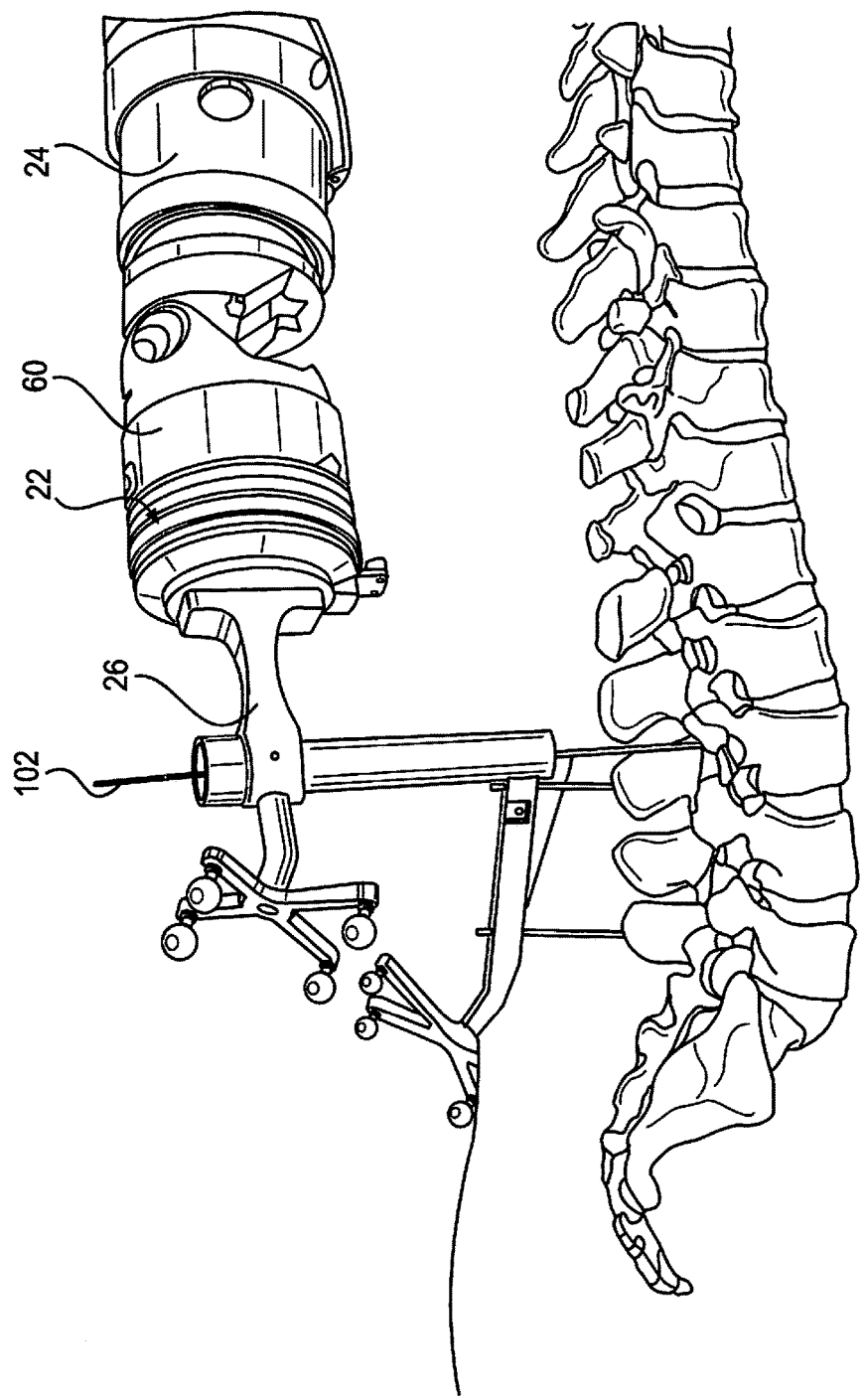
FIG. 12 illustrates an embodiment of a gravity well for a medical procedure.

During a medical operation, medical personnel may program robot support system 4 to operate within defined specifications. For examples, as illustrated in FIG. 12, a patient 50 may have a medical procedure performed upon the spine. Medical personnel may use imaging equipment to locate and find the spine, as detailed above. Using the images, an operator may upload the information regarding the location of the spine into automated medical system 2. Automated medical system 2 may then track, locate, and move end effector tools 26 to areas specified by the operator. In an example, a gravity well 102 and/or a plurality of gravity wells 102 may be mapped in relation to the spine of patient 50, as illustrated in FIG. 12. Gravity wells 102 may be virtual regions, programmed by an operator, that cause SCARA to function in a different mode once entered. Gravity wells 102 may be any suitable shape, including but not limited to conical, cylindrical, spherical, or pyramidal. These gravity wells may cause SCARA 24 and end effector 22 to move toward the direction, angle, and location programmed by medical personnel.

Figure 13:
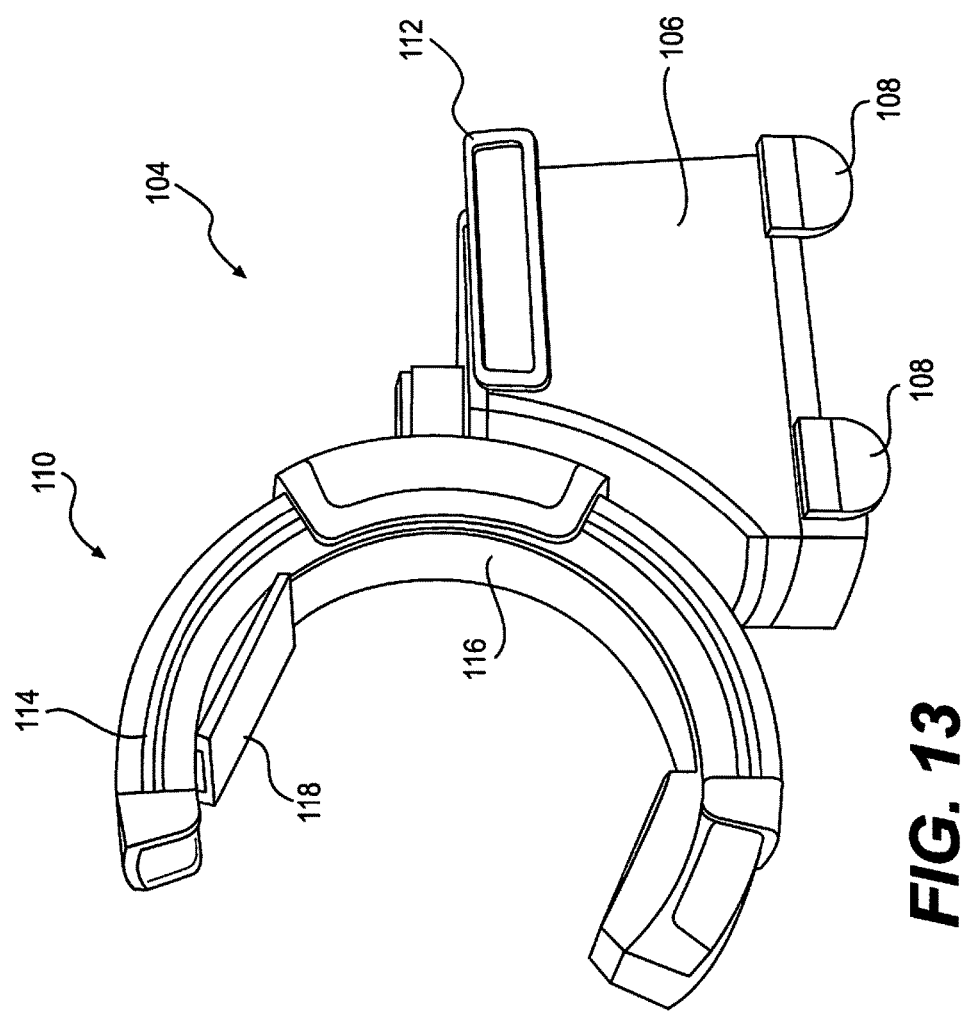
FIG. 13 illustrates an embodiment of an end effector tool moving toward a gravity well.
Figure 14:
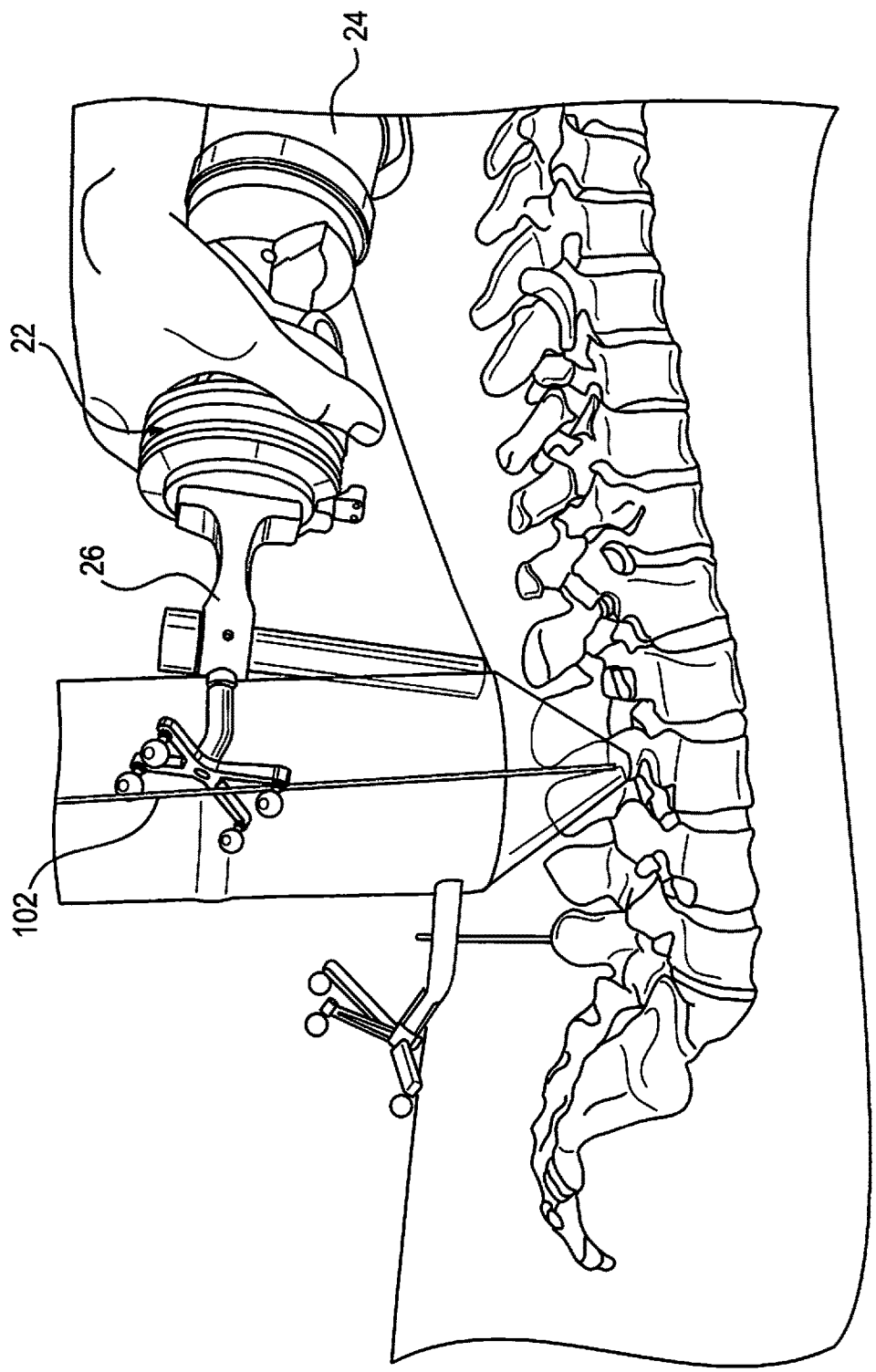
FIG. 14 illustrates an embodiment of an end effector tool positioned along a gravity well.

As illustrated in FIG. 13, the center line of a gravity well 102 indicates, in a virtual space, the angle and location end effector tool 26 may need to be positioned for a medical procedure. Alternately, any vector within the gravity well, not just the centerline, could be the target toward which the end effector tool is forced. End effector tool 26, as illustrated, may be moved by an operator using activation assembly 60, discussed above. As end effector tool 26 moves from outside the region of the gravity well to within the region of gravity well 102, the operator may feel the motors in SCARA 24 begin to move end effector tool 26 toward the programmed position of the centerline of gravity well 102. As illustrated in FIG. 14, gravity well 102 may maneuver end effector tool 26 into the programmed position. In an example, while end effector tool 26 is still in the gravity well, if the operator begins to move end effector tool 26 away from the center of the gravity well using activation assembly 60, the operator may feel the motors provide resistance against the movement. The resistance from the motors may not be strong enough resistance to keep end effector tool 26 within gravity well 102. This weak resistance may be beneficial as it may allow the operator to maneuver end effector tool 26 out of one gravity well and into any additional gravity well 102. The amount of force pulling the end effector toward the centerline of the gravity well 102 may be inversely proportional to the distance from the centerline. As an example, when first entering the gravity well, the operator may feel slight pull toward the centerline of the gravity well, and as the end effector tool 26 comes into closer proximity with the centerline of the gravity well, the magnitude of force may increase. Gravity well 102 may be programmed into automated medical system 2 before the medical operation and/or during the medical operation. This ability to adjust programming may allow medical personnel to move the centerline and/or change the volume of a gravity well 102 based on the changing conditions of the medical procedure. Gravity wells 102 may allow automated medical system 2 to place end effector tools 26 in the required area quickly, easily, and correctly.

Although the present invention and its advantages have been described in detail, it should be understood that various changes, substitutions and alterations may be made herein without departing from the spirit and scope of the invention as defined by the appended claims.

What is claimed is:

1. An apparatus, comprising:
   a robot arm;
   an end effector coupled at a distal end of the robot arm and configured to hold a surgical tool;
   a plurality of motors operable to move the robot arm; and
   an activation assembly operable to send a move signal allowing an operator to move the robot arm,
   wherein the activation assembly is in the form of a bracelet on the end effector.

2. The apparatus of claim 1, wherein the end effector further comprises a load cell operable to detect and measure force applied to the end effector.

3. The apparatus of claim 2, wherein the load cell is in communication with a motor driver of the plurality of motors by way of a microcontroller unit.

4. The apparatus of claim 2, wherein the microcontroller unit and/or a motion controller receive information on the force applied to the end effector measured by the load cell and control the plurality of motors to replicate the motion and direction of the force applied to the end effector.

5. The apparatus of claim 2, wherein the end effector comprises a saddle joint, the load cell being coupled to the saddle joint.

6. The apparatus of claim 1, wherein the activation assembly comprises a primary button and one or more primary activation switches, wherein primary button is disposed upon the one or more primary activation switches, wherein depression of the primary button is required to send the move signal.

7. The apparatus of claim 6, wherein the one or more primary activation switches comprises two or more primary activation switches activated by the primary button, wherein depression of at least two of the primary activation switches is required for the operator to move the robot arm.

8. The apparatus of claim 5, wherein the primary button comprises a ridge that encircles the end effector.

9. The apparatus of claim 5, wherein the activation assembly further comprises a secondary button operable to select functions, modes, and/or acknowledge information communicated to an operator.

10. The apparatus of claim 9, wherein the primary button comprises a ridge that encircles the end effector, and wherein the secondary button comprises a ridge that encircles the end effector.

11. A method of moving a robot arm comprising:

depressing a primary button on an activation assembly;

applying force to the activation assembly;

sensing the force with a load cell;

communicating force to a computer processor; activating motors within robot arm using the computer processor; and moving the robot arm with the motors in the direction of the applied force, wherein the primary button comprises a ridge encircling an end effector coupled to the robot arm, the end effector holding a surgical tool.

12. The method of claim 11, wherein depressing the primary button activates one or more primary activation switches.

13. The method of claim 12, wherein moving the robot arm requires activating of at least two primary activation switches.

* * * * *